United States Patent [19]
Coffey et al.

[11] Patent Number: 5,436,351
[45] Date of Patent: Jul. 25, 1995

[54] IMIDAZOLIDONE POLYETHERAMIDE SURFACTANT

[75] Inventors: David A. Coffey; Wei-Yang Su, both of Austin, Tex.

[73] Assignee: Huntsman Corporation, Salt Lake City, Utah

[21] Appl. No.: 112,295

[22] Filed: Aug. 27, 1993

[51] Int. Cl.$^6$ .......................................... C07D 233/32
[52] U.S. Cl. ............................... 548/324.1; 548/323.5
[58] Field of Search ............................ 548/324.1, 323.5

[56] References Cited

U.S. PATENT DOCUMENTS

| | | | |
|---|---|---|---|
| 3,116,967 | 1/1964 | Goldstein et al. | 8/115.6 |
| 3,226,379 | 12/1965 | Steyermark | 548/323.5 X |
| 3,347,926 | 10/1967 | Zech | 260/585 |
| 3,373,204 | 3/1968 | Hales et al. | 260/570.7 |
| 3,390,184 | 6/1968 | Moss et al. | 260/585 |
| 3,509,085 | 4/1970 | Sekmakas | 548/323.5 X |
| 3,654,370 | 4/1972 | Yeakey | 260/584 |
| 3,896,088 | 7/1975 | Raynolds | 548/323.5 X |
| 4,014,933 | 3/1977 | Boettger et al. | 260/563 |
| 4,152,345 | 5/1979 | Gaudette et al. | 260/439 |
| 4,153,581 | 5/1979 | Habermann | 252/472 |
| 4,358,389 | 11/1982 | König-Lumer et al. | 252/80 |
| 4,409,399 | 10/1983 | Swift et al. | 564/473 |
| 4,526,915 | 7/1985 | Sekmakas et al. | 544/316 X |
| 4,744,913 | 5/1988 | Salvador et al. | 252/80 |
| 4,766,245 | 8/1988 | Larkin et al. | 564/474 |
| 4,883,873 | 11/1989 | Abboud et al. | 544/316 |
| 4,954,279 | 9/1990 | Ma et al. | 252/70 |
| 4,973,761 | 12/1990 | Schoenleben et al. | 564/475 |
| 5,003,107 | 3/1991 | Zimmerman et al. | 564/475 |
| 5,118,434 | 6/1992 | Meyer et al. | 252/70 |
| 5,118,435 | 6/1992 | Nieh | 252/70 |
| 5,288,873 | 2/1994 | Su et al. | 548/323.5 |

FOREIGN PATENT DOCUMENTS 1556612 2/1969 France .
1130822 6/1962 Germany .

OTHER PUBLICATIONS

Glass, J. Edward, ed., *Polymers in Aqueous Media: Performance Through Association*, Lochhead et al., "Poly(acrylic acid) Thickeners: The Importance of Gel Microrheology and Evaluation of Hydrophobically Modified Derivatives as Emulsifiers", pp. 113–147 (1989).

Friberg, Stig E. and Becher, Paul, eds. *Journal of Dispersion Science and Technology*, Schosseler et al., "Swelling Kinetics of Small Spherical Ionic Gels", pp. 321–339 (1987).

Yasaka, M., et al., "1,3-Dimethyl-2-imidazolidinone" Chemical Abstracts, vol. 90, abstract 90:72186w, 1970.

*Primary Examiner*—Jacqueline Haley
*Attorney, Agent, or Firm*—Russell R. Stolle; Ron D. Brown

[57] ABSTRACT

Disclosed is a novel composition of the formula:

$$R^5\underset{H}{\overset{O}{\underset{\|}{N}}}\overset{R}{\underset{}{\diagup}}\left(O\overset{R}{\underset{}{\diagup}}\right)_{a-1}\underset{\underset{O}{\|}}{N}\overset{R}{\underset{}{\diagdown}}N\diagup\diagdown O\left(\overset{R}{\underset{}{\diagup}}O\right)_{b-1}\overset{R}{\underset{\underset{O}{\|}}{\diagup}}\underset{H}{\overset{}{\underset{}{N}}}R^5$$

wherein R=H, methyl, ethyl, or a mixture thereof and $R^5$=a saturated or unsaturated alkyl group from a fatty acid containing 7 to 22 carbon atoms and a+b=n, wherein n is from about 2 to 80, resulting from alkoxylating an substituted imidazolidone, reductively aminating the alkoxylated product and reacting the aminated product with a fatty acid; and, to its use as a surfactant in glycol-water mixtures, such as, for example, propylene glycol based wing deicers thickened with polyacrylic acids.

2 Claims, No Drawings

IMIDAZOLIDONE POLYETHERAMIDE SURFACTANT

CROSS-REFERENCE

This application is related to U.S. patent application Ser. No. 07/928,582, now U.S. Pat. No. 5,288,873.

FIELD OF THE INVENTION

This invention relates to anti-icing compositions. More particularly this invention relates to a novel polyetheramide surfactant and to its use in alkylene glycol based wing deicers thickened with polyacrylic acids to produce a deicing fluid having the potential for providing significant ice protection when used on airplane wings in freezing rain conditions.

BACKGROUND OF THE INVENTION

Liquid substances applied to the airfoil surfaces of aircraft to prevent their freezing and being covered with ice in inclement weather are well-known and are important to ensure safe and proper takeoff of aircraft in winter. It is also well-known that aircraft departures are often delayed under such conditions and the anti-icing formulations must often be reapplied if the plane must wait an extended period. These liquids must also be stable not only through temperature extremes, but also during the taxiing phases of the takeoff procedure and thus must adhere to the wing surfaces during travel and ground winds.

Deicing solutions based upon ethylene glycol and water have been used for many years to remove ice, frost and snow from aircraft surfaces, however, since they have low viscosities, they readily flow off the aircraft surfaces and thus provide limited protection from formation of additional frost.

Anti-icing fluids are those that will prevent formation of frost and ice on surfaces over extended periods such as overnight and in the case of delays between departure from the gate and takeoff.

One approach to formulating anti-icing fluids is to add thickening agents to deicing fluids with the intention of increasing the viscosity of the fluid and thereby reducing its tendency to run off the surfaces of the aircraft. There are a number of thickened fluids which are commercially available. These include Kilfrost Anti-Icing Fluid ABC-3, SPCA AD-104, Union Carbide UC 5.1 and Octagon 40 below.

A good anti-icing fluid must be readily removed from the surfaces of the aircraft during takeoff. It should also have good rheological properties in that it must have sufficient viscosity to be retained on the aircraft surface yet require little force to be removed. It is also important that it can be applied with conventional spraying devices without causing undue shear instability and loss of thickening properties.

In addition, the agent should not have a tendency to thicken during storage, so that when it is applied it is too viscous for effective removal or that the gelling results in phase separation, causing a loss of anti-icing properties.

Other anti-icing compositions are known. For example, a liquid agent for deicing and protecting against icing-up is described in U.S. Pat. No. 4,358,389 by means of which it is possible, in particular, to free the metal surface of aircraft rapidly and completely from ice, hoar-frost, snow and the like and to protect the surface against further build-up for a relatively long period. The agent is essentially composed of several components, namely of (a) glycols, (b) water, (c) thickeners, (d) substances insoluble in water, (e) surface-active agents, (f) corrosion inhibitors and (g) alkaline compounds. The quantities are very specific in each case, the quantity of the components (a) and (b) being at least 94%, relative to the total weight of the agent. The pH value is 7.5 to 10. Component (c) is cross-linked polyacrylate thickeners described in that patent and in U.S. Pat. No. 2,923,692.

U.S. Pat. No. 4,744,913 describes an anti-icing and deicing agent, based on glycols and water and having cross-linked acrylic polymers useful as thickeners and also containing customary corrosion inhibitors, surfactants belonging to the group of alkali metal alkylarylsulfonates and a neutralizing agent to adjust the pH to a basic value.

The agent contains as a thickener, two selected cross-linked acrylic polymers in a specific ratio by weight to one another, namely a selected cross-linked acrylic acid/aryl amide or alkali metal acrylate/acrylamide copolymer in a ratio by weight of 2:1 to 10:1. The neutralizing agent may be one of three compounds, ammonia, monoethanolamine, diethanolamine and/or triethanolamine as the first alkaline compound, potassium hydroxide as the second alkaline compound and a third alkaline compound. The composition of that invention is claimed to have relatively low viscosity even at arctic temperatures and low shear rates which ensures rapid and complete runoff of the agent at the takeoff of aircraft even under extreme conditions.

In U.S. Pat. No. 4,954,279 there is disclosed a deicer and anti-icing composition comprising a microemulsion having a continuous phase and a discontinuous phase comprising: 5 to 85% by weight glycol, 5% to 95% water, 5.0% by weight water insoluble oil comprising 0.1 to 2.5% polar compound and the remainder including a thickening agent, an emulsifier, and alkanolamines. It is stated that the composition provides desirable viscosity and shear stability.

U.S. Pat. No. 5,118,435 discloses an antifreeze composition that can retain high viscosity as the composition is diluted with water, is claimed to have highly pseudoplastic rheology so that it would have desirable flow off characteristics and is relatively insensitive to temperature changes over the range −25° C. to 20° C. This composition contains an alkylene glycol component, a thickener blend with at least one polyacrylic acid and at least one copolymer of acrylic acid, a hydrophilic vinyl monomer and an agent to neutralize at least part of the carboxylic acid groups present in the polymers of the thickener blend.

Partially neutralized polymers of acrylic acid forming water swellable networks with high water retention capability and very fast kinetics of volume change have been reported by F. Schosseler, et al. in *J. Dispersion Sci. Technol.*, Vol. 8, p. 321, 1987. Further information about polyacrylic acids may be found in R. B. Lochhead, et al., "Polyacrylic acid thickener: The importance of gel microrheology and evaluation of hydrophobe modified derivative as emulsifier." *Polymers in Aqueous Media*, J. E. Glass, Editor, Advances in Chemistry Series. #223.

It is known in the art to aminate long alkoxylated alkyl chains terminated by hydroxyl groups. U.S. Pat. No. 3,654,370 to E. L. Yeakey teaches the amination of polyoxyalkylene polyols.

U.S. Pat. No. 5,288,873 relates to a process for making novel polyetherdiamines containing a cyclic urea from imidazolidones. The products of that invention were useful alone or in combination with known polyoxyalkyleneamines as curing agents.

In the instant invention the polyetherdiamine of U.S. Pat. No. 5,288,873 is reacted with certain fatty acids to produce a polyetheramide surfactant, useful as a surfactant in glycol-water mixtures.

There is always a need in the art of thickened aircraft anti-icing compositions for improvements which allow for compositions exhibiting advantageous rheological properties and which under low shear conditions are relatively insensitive to temperature changes. Other advantageous properties are retention of high viscosity even if diluted with water and stability for relatively long periods to delay or avoid reapplications of the composition during departure holdovers.

SUMMARY OF THE INVENTION

This invention relates to the preparation of a polyetheramide of the formula:

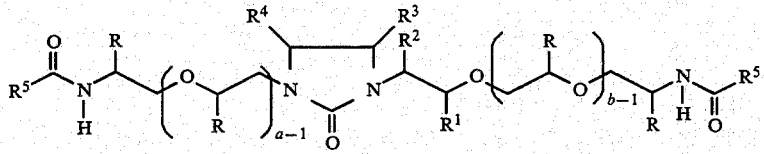

where R=H, methyl, ethyl or a mixture thereof, $R^1$, $R^2$, $R^3$ and $R^4$ are selected from the group consisting of hydrogen and lower alkyl radicals having from about 1 to 4 carbon atoms and $R^5$=an alkyl group containing 7 to 22 carbon atoms from a fatty acid and a+b=n=the number of moles of alkylene oxide used in the alkoxylating step. This polyetheramine has been found useful as a surfactant in the type of alkylene glycol-based wing deicers which are thickened with polyacrylic acids.

DETAILED DESCRIPTION OF TEE INVENTION

The process for preparing the compounds of this invention comprises:

1. Preparation of hydroxyalkyl-2-imidazolidones from urea, and the corresponding aminoalkylalkanolamine represented by:

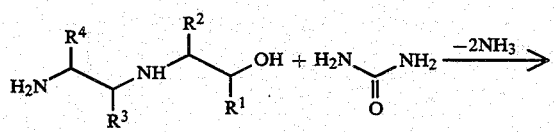

-continued

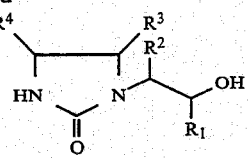

It may be noted that other possible feedstock which can be used instead of urea include dimethyl carbonate and ethylene carbonate.

2. Alkoxylation of a 1-2'-hydroxyalkyl-2-imidazolidone with an alkylene oxide to produce a polyol, as represented by:

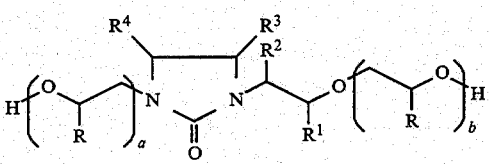

3. Reductive amination of the polyol of (2) to form a novel polyetherdiamine containing an imidazolidone and, therefore, a cyclic urea, as represented by:

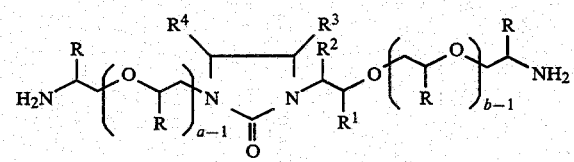

wherein $R^1$, $R^2$, $R^3$, and $R^4$ are selected from the group consisting of hydrogen and lower alkyl radicals having from about 1 to 4 carbon atoms, R is H or an alkyl group of from 1 to 16 carbon atoms, and a+b=n, wherein n is from about 2 to 80. Steps 1→3 are described in U.S. Pat. No. 5,288,873 incorporated herein by reference in its entirety. This step generally takes place at temperatures from 180° C. to 240° C.

4. The novel aspect of the instant invention comprises reacting the aminated alkylene oxide adduct of 1-2'-hydroxyethyl-2-imidazolidone with a fatty alkyl acid of the formula:

$R^5$COOH where $R^5$ is a saturated or unsaturated alkyl group containing 7 to 22 carbon atoms, resulting in a polyetheramide of the formula:

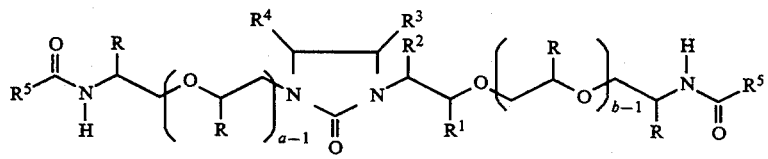

where R=H, methyl, ethyl or a mixture thereof, $R^1$, $R^2$, $R^3$ and $R^4$ are selected from the group consisting of hydrogen and lower alkyl radicals having from about 1 to 4 carbon atoms and $R_5$=an alkyl group containing 7 to 22 carbon atoms from a fatty acid.

The composition of the invention is useful in glycol-water mixtures to enhance wetting ability.

In particular, the composition would be useful as a surfactant in alkylene glycol-based wing deicers which are usually thickened with polyacrylic acids. The polyetheramide surfactants may also be useful in other types of lubricants and coatings.

The complex sequence for preparing the novel polyetheramide surfactant, imidazolidone containing polyetherdiamines, starting with the substituted imidazolidone, can be represented best by the following:

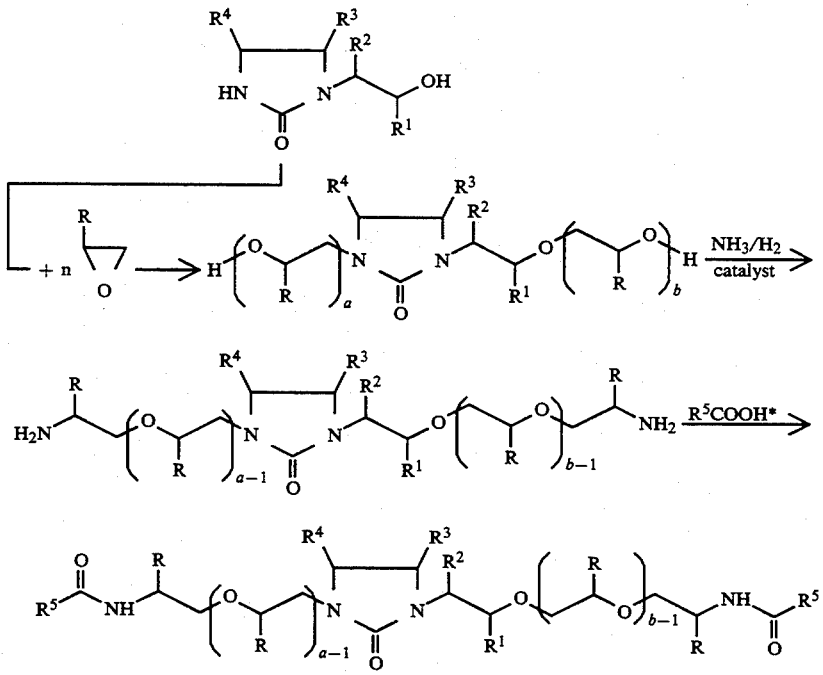

where R is H or an alkyl of 1 to 4 carbon atoms, $R^1$, $R^2$, $R^3$ and $R^4$ are selected from the group consisting of hydrogen and lower alkyl radicals having about from 1 to 4 carbon atoms, n is the number of moles of alkylene oxide employed in alkoxylation and a+b=n, wherein n is from about 2 to 80.

The initiator, 1-hydroxyalkyl-2-imidazolidone, can be easily prepared by reacting urea, dimethyl carbonate, ethylene carbonate or propylene carbonate with the corresponding aminoalkylalkanolamine and is represented by the structure:

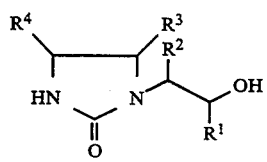

wherein $R^1$, $R^2$, $R^3$ and $R^4$ are selected the group of hydrogen and lower alkyl radicals having from 1 to 4 carbon atoms. Examples of 1-2'-hydroxyalkyl-2-imidazolidones that are suitable initiators in the desired synthesis of polyols include 1-2'-hydroxyethyl-2-imidazolidone (HEIMD), 1-2'-hydroxypropyl-2-imidazolidone, 1-2'-hydroxyethyl-4-methyl-2-imidazolidone, 1-2'-hydroxyethyl-5-methyl-2-imidazolidone, 1-2'-hydroxyethyl-4,5-dimethyl-2-imidazolidone, 1-2'-hydroxypropyl-4, 5-dimethyl-2-imidazolidone and 1-2'-hydroxy-1'-methylpropyl-2-imidazolidone.

The alkoxylation reaction employed to prepare the alkylene oxide adduct of the cyclic urea initiator utilized to prepare the compounds of this invention is carried out according to methods well-known in the art, as described in U.S. Pat. No. 5,288,873.

The alkoxylation proceeds using alkylene oxides containing 2 to 6 carbon atoms, or combinations thereof. Particularly suitable are ethylene oxide, propylene oxide and butylene oxide or combinations thereof. Variations in the number of moles of alkylene oxides or mixtures thereof used in alkoxylation result in predictably different hydroxyl number products, expressed as mg KOH/g, for the resulting polyols.

The alkoxylated substituted HEIMD products are converted to the corresponding primary amines by reaction with ammonia over a hydrogenation/dehydrogenation catalyst. Generally reductive amination catalysts are composed primarily of nickel, cobalt or copper, or these metals in combination as the active components. The catalyst can contain other metals as well, such as iron, zinc, chromium, manganese, zirconium, molybdenum, tungsten, rhenium, and ruthenium. Other promoters such as barium, magnesium, and phosphorous have been used in reductive amination catalysts. Precious metals such as platinum and palladium have also been used in some catalysts. The catalysts can be unsupported or supported. Common supports that have been used for these catalysts include alumina, silica, silica-alumina, zirconia, magnesia, and titania. This is discussed in detail in U.S. Pat. No. 5,288,873.

The focus of the instant invention is the reaction of the polyetherdiamine with a carboxylic acid of the formula $R^5COOH$ derived from or contained in an animal or vegetable fat or oil. $R^5$ represents an alkyl group containing 7 to 22 carbon atoms. The fatty acid may be saturated or unsaturated. Examples of saturated fats include, but are not limited to, lauric ($C_{12}$), palmitic ($C_{16}$) and stearic ($C_{18}$). No catalyst is required for the reaction of this invention. The fatty acids may also be unsaturated. These acids are usually vegetable derived and consist of alkyl chains containing 18 or more carbon atoms. Most vegetable oils are actually mixtures of several fatty acids or their glycerides. The most common unsaturated acids are oleic, linoleic and linoleic.

One fatty acid which is exemplified herein is that derived from coconut oil, containing 12 to 15 carbons, comprised of glycerides of lauric, capric, myristic, palmitic and oleic acids.

Another exemplified fatty acid is oleic, $CH_3(CH_2)_7CH:CH(CH_2)_7COOH$, a monounsaturated fatty acid component of almost all natural fats as well as tall oil.

The temperature for the reaction should be in the range of 90° C. to 200° C. and is preferably from 125° to 180° C.

The pressure should be in the range from 0 to 500 psig and preferably from 0 to 100 psig.

Typical deicing and anti-icing agents for aircraft, based on glycols and water are essentially composed of:
 (a) 40% to 70% by weight of a glycol belonging to the group of alkylene glycols having 2 to 3 carbon atoms and oxyalkylene glycols having 4 to 6 carbon atoms.
 (b) 0.1% to 1.0% by weight, cross-linked acrylic polymers
 (c) 0.05% to 1% by weight of a surfactant
 (d) 0.1% to 1% by weight corrosion inhibitor
 (e) an amine (optional)
 (f) potassium hydroxide (optional)
 (g) alkalai metal hydroxide
 (h) water A good discussion of the various components and suitable quantities of each is found in U.S. Pat. No. 5,118,435, incorporated herein by reference in its entirety.

The focus of the instant invention is its preparation and use of a novel polyetheramide as a surfactant in a deicing or anti-icing agent. The polyetheramide surfactant of the instant invention contains an ethylene urea (2-imidazolidone) linkage. It should be useful in glycol-water mixtures to enhance wetting ability. It may also be useful in other types of lubricants or coatings.

A surfactant is an optional component in some deicing or anti-icing agents in the art. Where employed it is often found that a nonionic surfactant can improve the wetting of the aircraft surface. The surfactant is preferably employed in an amount between 0.1 to 5.0 by weight based on total composition.

When used as a surfactant in appropriate amounts in a deicing agent, for example, the instant polyetheramide gave a very nearly flat viscosity temperature profile from 20° C. to −20° C. using Brookfield spindle SC4-31/13R (rotation speed 0.3 rpm). A deicing fluid containing this surfactant has the potential to provide significant ice protection when used on airplane wings (or other surfaces) in freezing rain conditions.

In Examples 4 and 5 two deicing blends were prepared and adjusted to the same viscosity. Then the polyetheramide surfactants of this invention were added in an amount of about 0.5% in each blend. In Example 4 the alkyl group was from coconut acid and in Example 5 the alkyl group was from oleic acid.

When employed in small amounts as surfactants in deicing and anti-icing blends the polyetheramide surfactants of the instant invention, incorporating fatty acid alkyl groups, provide compositions which retain high viscosity when diluted with water. Additionally, they exhibit a highly pseudoplastic rheology, indicating that they possess desirable flow off characteristics. That is, the compositions will be retained on aircraft surfaces for sufficiently long periods, but will liquify under relatively high shear conditions. This viscosity under low shear conditions for these materials is relatively insensitive to temperature changes between about −25° C. and about 20° C. This feature will allow a relatively predictable thickness of the fluid to be applied to the aircraft and lead to predictability in holdover time over a wide range of temperatures. It is important that anti-icing compositions be as stable as possible between applications and aircraft departure, even if this is an extended time period under adverse conditions. The materials produced using the surfactants of this invention show good properties for the needed stability in these environments.

The examples which follow are only for the purpose of illustration. It is understood that they are not intended to limit the invention in any way.

EXAMPLE 1 (6835-74)

A one-liter three-necked flask equipped with a thermometer, Dean-Stark trap, stirrer and nitrogen inlet was charged 250 g of an aminated block 10-mole ethylene oxide and 3-mole of propylene oxide adduct of 1-2'-hydroxyethyl-2-imidazolidone and 133.5 g of water generated was removed through the Dean-Stark trap. The resulting product (371.5 g) was a yellow liquid and water soluble.

EXAMPLE 2 (6835-75)

The procedure of Example 1 was followed except that 200 g of an aminated block 10-mole of ethylene oxide and 3-mole of propylene oxide adduct of 1-2'-hydroxyethyl-2-imidazolidone and 140 g of oleic acid were used. The resulting product (330 g) was a light brown liquid and water soluble.

EXAMPLE 3 (6834-76)

The procedure of Example 1 was followed except that 200 g of an aminated block 4-mole of ethylene oxide and 2-mole of propylene oxide adduct of 1-2'-hydroxyethyl-2-imidazolidone and 130 g of coconut acid were used. The resulting product (318 g) was a light brown liquid and water soluble.

EXAMPLE 4 (6856-64)

A composition consisting of a 3% aqueous solution of CARBOPOL ® 672 and 1621 polyacrylic acid resins in a 95:5 ratio (64.2 g), propylene glycol (311.0 g), COBRATEC® TT-50S tolyltriazol solution (3.0 g), 6835-74 (Example 1) (3.0 g), 2% aqueous solution of NaOH (27.9 g) and deionized water (191.9 g) was prepared. The viscosity of this blend was 2700 cP at 0° C., 0.3 rpm on Brookfield spindle SC4-31/13R. Another blend was prepared with the same amounts except that 3.0 g of the 2% NaOH solution was replaced with deionized water. This gave a 7200 cP blend under the same conditions. These two blends were combined until a 6000 cP blend at 0° C. was derived. The resulting product was a slightly cloudy, colorless solution. The attached Tables I and II show how the blend's viscosity varies with temperature, shear rate and water dilution. When sheared at 3500 rpm at 20° C. for five minutes using a Brookfield counter-rotating mixer, the fluid exhibits no noticeable loss in viscosity at 0° C.

TABLE I

Example 4 (6856-64-3) - Unsheared Fluid
Viscosity (cP) as a Function of Temperature

| Temp. °C. | RPM, Brookfield spindle SC4-31/13R | | | | | | |
|---|---|---|---|---|---|---|---|
| | 0.3 | 0.6 | 1.5 | 3.0 | 6.0 | 12.0 | 30.0 |
| +20 | 6200 | 4100 | 2480 | 1750 | 1250 | 910 | 613 |
| 0 | 6000 | 4200 | 2860 | 2120 | 1600 | 1220 | 863 |
| −10 | 6800 | 5100 | 3440 | 2580 | 2040 | 1588 | — |
| −20 | 5800 | 4600 | 3220 | 2570 | 2060 | 1670 | — |

TABLE II

Example 4 (6856-64-3) - Sheared Fluid
Viscosity (cP) as a Function of Water Dilution at 0° C.

| Water % | RPM, Brookfield spindle SC4-31/13R | | | | | | |
|---|---|---|---|---|---|---|---|
| | 0.3 | 0.6 | 1.5 | 3.0 | 6.0 | 12.0 | 30.0 |
| 0 | 6000 | 4300 | 2840 | 2100 | 1570 | 1200 | 850 |
| 5 | 8800 | 5950 | 3800 | 2720 | 1980 | 1470 | — |
| 15 | 12800 | 8650 | 5140 | 3550 | 2520 | 1810 | — |
| 25 | 12100 | 7950 | 4790 | 3270 | 2310 | 1650 | — |

EXAMPLE 5 (6856-66)

A composition was prepared containing 3% aqueous solution of CARBOPOL ®672 and 1621 polyacrylic acid resins in a 95:5 ratio (64.2 g), propylene glycol (311.0 g), COBRATEC® TT-50S (3.0 g), 6835-75 (Example 2) (3.0 g), 2% aqueous solution of NaOH (27.5 g) and deionized water (191.3 g) was prepared. The viscosity of this blend was 2400 cP at 0° C., 0.3 rpm on Brookfield spindle SC4-31/13R. Another blend was prepared with the same amounts except that 2.6 g of 2% NaOH solution was replaced with deionized water. This gave a 9600 cP blend under the same conditions. These blends were combined until a 6000 cP blend was derived. The resulting product was a slightly cloudy, colorless solution. The attached Tables III and IV show how the blend's viscosity varies with temperature, shear rate and water dilution.

TABLE III

Example 5 (6856-66-3) - Unsheared Fluid
Viscosity (cP) as a Function of Temperature

| Temp. °C. | RPM, Brookfield spindle SC4-31/13R | | | | | | |
|---|---|---|---|---|---|---|---|
| | 0.3 | 0.6 | 1.5 | 3.0 | 6.0 | 12.0 | 30.0 |
| +20 | 5500 | 3600 | 2240 | 1600 | 1160 | 855 | 576 |
| 0 | 6000 | 4300 | 2880 | 2160 | 1630 | 1250 | 889 |
| −10 | 5300 | 4100 | 2910 | 2240 | 1770 | 1410 | — |
| −20 | 3300 | 2800 | 2180 | 1850 | 1570 | 1320 | — |

TABLE IV

Example 5 (6856-66-3) - Sheared Fluid
Viscosity (cP) as a Function of Water Dilution at 0° C.

| Water % | RPM, Brookfield spindle SC4-31/13R | | | | | | |
|---|---|---|---|---|---|---|---|
| | 0.3 | 0.6 | 1.5 | 3.0 | 6.0 | 12.0 | 30.0 |
| 0 | 6000 | 4300 | 2820 | 2090 | 1580 | 1210 | 857 |
| 5 | 8800 | 6100 | 3880 | 2800 | 2040 | 1520 | — |
| 15 | 14600 | 9600 | 5720 | 3950 | 2790 | 2000 | — |
| 25 | 13500 | 8920 | 5300 | 3680 | 2570 | 1830 | — |

What is claimed is:
1. A polyetheramide, having the following formula:

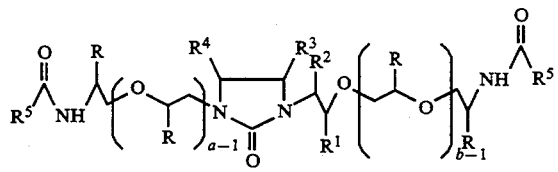

where each R is independently H, methyl or ethyl and wherein $R^5$ is independently a saturated or unsaturated alkyl group of 7 to 22 carbon atoms, $R^1$, $R^2$, $R^3$ and $R^4$ are selected from the group consisting of hydrogen and lower alkyl radicals having about 1 to 4 carbon atoms, and $a+b=n$, wherein n is from about 2 to 80.

2. The polyetheramide of claim 1 wherein each $R^5$ is independently a saturated or unsaturated alkyl group of 12 to 17 carbon atoms.

* * * * *